United States Patent [19]
Nakabayashi et al.

[11] Patent Number: 5,879,663
[45] Date of Patent: Mar. 9, 1999

[54] DENTAL COMPOSITION FOR DENTIN HYPERSENSITIVITY

[75] Inventors: Nobuo Nakabayashi, 5-6-20, Koganehara, Matsudo-shi, Chiba 270; Takashi Yamamoto, Moriyama; Yasukazu Saimi, Moriyama; Masami Arata, Moriyama; Harumi Tanaka, Moriyama, all of Japan

[73] Assignees: Sun Medical Co., Ltd., Moriyama, Japan; Nobuo Nakabayashi, Matsudo, Japan

[21] Appl. No.: 687,521

[22] PCT Filed: Dec. 7, 1995

[86] PCT No.: PCT/JP95/02511

§ 371 Date: Aug. 7, 1996

§ 102(e) Date: Aug. 7, 1996

[87] PCT Pub. No.: WO96/17581

PCT Pub. Date: Jun. 13, 1996

[30] Foreign Application Priority Data

Dec. 7, 1994 [JP] Japan .................................. 6-303848

[51] Int. Cl.$^6$ .............................. A61K 6/00; A61K 7/22; A61K 9/10
[52] U.S. Cl. ................................. 424/54; 424/49; 424/55; 424/56; 424/57; 424/401; 424/678; 424/682; 424/710; 106/35; 433/228.1
[58] Field of Search ................... 424/56, 49, 54, 424/55, 57, 401, 710, 678, 682; 106/35; 433/228.1

[56] References Cited

U.S. PATENT DOCUMENTS

| | | | |
|---|---|---|---|
| 4,057,621 | 11/1977 | Pashley et al. | 424/49 |
| 4,159,317 | 6/1979 | Onisi et al. | 424/50 |
| 4,538,990 | 9/1985 | Pashley | 433/217.1 |
| 5,234,971 | 8/1993 | Imai et al. | 424/57 |
| 5,538,883 | 7/1996 | Nishimoto et al. | 435/200 |
| 5,554,669 | 9/1996 | Nakabayashi et al. | 523/118 |
| 5,718,885 | 2/1998 | Gingold et al. | 424/49 |
| 5,766,328 | 6/1998 | Nakabayashi et al. | 106/35 |
| 5,780,015 | 7/1998 | Fisher et al. | 424/52 |

FOREIGN PATENT DOCUMENTS

| | | |
|---|---|---|
| 48-79489 | 10/1973 | Japan . |
| 4217904 | 8/1992 | Japan . |
| 5-70358 | 3/1993 | Japan . |
| 5105611 | 4/1993 | Japan . |
| 5255029 | 10/1993 | Japan . |
| 6-57080 | 3/1994 | Japan . |
| 6116153 | 4/1994 | Japan . |
| 6145020 | 5/1994 | Japan . |

OTHER PUBLICATIONS

Derwent Abstract, accession number 93–172615; abstracting JP 5–105611 (Apr., 1993).

*Primary Examiner*—John Pak
*Attorney, Agent, or Firm*—Sherman and Shalloway

[57] ABSTRACT

There is provided a dental composition for relieving dentin hypersensitivity, which occludes dentinal tubules having an opening on the surface of dentin to relieve dentin hypersensitivity thereby to give an immediate relieving effect and to maintain the relieving effect for a long time.

The dental composition for relieving dentin hypersensitivity, which comprises (A) a low molecular weight compound which can produce a precipitate which is hardly soluble in water when it reacts with a calcium compound, or which comprises the above component (A), (B) a calcium compound and/or (C) an aqueous polymer emulsion having a particle size smaller than that of a dentinal tubule and forming an agglomerate or a hardly soluble gel larger than the diameter of a dentinal tubule when it reacts with a calcium compound.

37 Claims, No Drawings

DENTAL COMPOSITION FOR DENTIN HYPERSENSITIVITY

This application is a 371 of PCT/JP95/02511 filed on Dec. 7, 1995.

1. Technical Field

This invention relates to a dental composition for occluding dentinal tubules. More specifically, it relates to a dental composition for relieving dentin hypersensitivity which induces pain sensations such as cold water, hot water, sweet, acidity and scraping pain sensations, by occluding dentinal tubules. Further, it relates to a dental composition which can be preserved stably and hygienically.

2. Background Art

Cold and heat pain sensations which are encountered when a tooth is brought into contact with air or water having different temperature from body temperature, sweet and acidity pain sensations which are encountered when sweet or acidic foods are taken, and a scraping pain sensation which is encountered when a tooth is brought into contact with a toothbrush or the like are caused by dentin hypersensitivity or pulpitis.

Pulpitis occurs as a result of inflammation caused by the infection of dental pulp with microbes, and its pain sensation continues for a relatively long period and can be treated only by removing the dental pulp.

Meanwhile, dentin hypersensitivity is a temporary induced pain sensation produced by physical or chemical stimulus. Therefore, a technique for easing the nerve cell of pulp whose reaction to stimulus is hypersensitive and a technique for excluding external stimulus to dental pulp have been proposed as a technique to overcome dentin hypersensitivity.

Pashley et al. propose in the specification of U.S. Pat. No. 4,057,621 a dental composition for relieving hypersensitivity which comprises an oxalate of a mono- or bi-substituted alkali metal or ammonium in a concentration range of from 2% by weight to saturation as well as a technique for relieving hypersensitivity.

In Japanese laid-open patent application publication No.4-217904, Imai et al. propose a dental treatment composition for forming a precipitate by sequentially applying two liquids A and B containing substances which produce a hardly soluble precipitate when mixed together. In this proposal, the liquid A is an aqueous solution containing 1 to 70% of a sodium salt, potassium salt or lithium salt of an inorganic or organic acid, and the liquid B is an aqueous solution containing 1 to 70% of a mixture containing at least one selected from the group consisting of chlorides, nitrates, sulfates and acetates of calcium, zinc, strontium, magnesium, aluminum, barium, iron, copper, silver, lead and tin, or calcium chloride, zinc chloride or strontium chloride.

Japanese laid-open patent application publication No.6-145020 proposes a crystal-forming primer for tooth, which comprises (A) a solution of 1 to 35% potassium oxalate, (B) aluminum oxalate and (C) 2% nitric acid.

Japanese laid-open patent application publication NO.5-70358 proposes a treatment agent for dentin hypersensitivity containing the following components (A) and (B). The component (A) is a colloidal zinc hydroxide and/or zinc oxide obtained by mixing a water-soluble zinc salt and a polyol phosphoric acid ester and/or a salt thereof in an aqueous medium, and the component (B) is a zinc salt of a polyol phosphoric acid ester.

In Japanese laid-open patent application publication No.5-255029, Imai et al. propose a dental treatment composition for forming a precipitate by sequentially applying two liquids A and B containing substances capable of producing fluoroapatite swiftly when mixed together. In this respect, the liquid A contains a water-soluble phosphoric acid salt in a concentration range of 1 to 30% and a water-soluble fluoride in an amount of 0.01 to 5% by weight, and the liquid B contains a water-soluble calcium salt in an amount of 1 to 30% by weight.

Japanese laid-open patent application publication No.6-116153 proposes a coating agent for relieving hypersensitivity which consists of a first liquid containing an aluminum compound and a second liquid containing at least one compound selected from the group consisting of phosphoric acid compounds, oxalic acid compounds, silicic acid compounds, fluorides and compounds providing alkalinity. This proposal is aimed to precipitate a deposit in dentinal tubules which are open to the exposed surface of dentin and occlude the dentinal tubules by applying a solution of a compound or composition for forming a deposit onto the surface of a tooth. It also makes use of the effect of relaxing the activity of sensory nerves with a certain compound such as a potassium ion.

However, it has been difficult to newly form on the surface of dentin a predetermined amount of a precipitate large enough to occlude a dentinal tubule which is said to have a diameter of 1 to 3 μm because of impedient conditions such as the properties of a tooth and a sanitary state of the surface of dentin. To attain this purpose, methods in which a long-time treatment or repetitions of a treatment are required have been employed and accordingly, patients have suffered more pain in these treatments.

A technique for easing the nerve cell of pulp is aimed to paralyze or ease the nerve cell which is made hypersensitive by a medicine or the like. However, its mechanism has not been elucidated thoroughly. One of the means of excluding external stimuli from dental pulp is to occlude a dentinal tubule for connecting the outside and the dental pulp, and as described above, there is a proposal for causing a precipitate to occlude dentinal tubules with the precipitate formed on the surface of a tooth. However, formation of a precipitate or precipitation of a precipitate into a dentinal tubule could not be carried out satisfactorily depending on the opening conditions of the dentinal tubule near the surface of dentin and the properties of a tooth, thereby making it impossible to keep occlusion stably for a prolonged time.

In Japanese laid-open patent application publication No.6-57080, Nakabayashi et al. propose an emulsion of an emulsified polymer which comprises a recurring unit derived from a (meth)acrylic acid ester and a recurring unit derived from a vinyl compound having a functional group —$SO_3R$ (R is a hydrogen atom, an alkali metal or ammonium ion) and a method for relieving dentin hypersensitivity using the same. Advantages obtained by applying a polymer emulsion to dentin hypersensitivity are that a large amount of a polymer can be applied with a relatively low viscosity liquid and that the polymer becomes insoluble in water when it is dried to be formed into a film. In particular, since a solvent for an aqueous emulsion of a polymer is water, there are almost no handling problems such as toxicity and ventilation.

DISCLOSURE OF THE INVENTION

The inventors of the present invention have conducted additional experiments based on the above proposal made by Nakabayashi et al., and have observed the effect of relieving hypersensitivity in 15 out of 17 patients having dentin hypersensitivity. However, a remarkable relieving effect was not observed in the remaining 2 patients. The inventors have conducted intensive studies on the cause of no effect and found that the amount of an emulsion charged into a dentinal tubule and the stability (retention) of a formed film differ depending on the opening conditions of the dentinal tubule and the location and properties of dentin. In other words, when the opening of the dentinal tubule is small, the emulsion can not be sometimes sufficiently charged into the tubule. Further, it has been revealed that in the case of tooth having a small content of hydroxyapatite such as deep dentin and root dentin, adhesion of the formed film to the surface of dentin and retention of adhesion may be insufficient in some cases.

It is therefore an object of the present invention to provide a dental composition which is for use in relieving dentin hypersensitivity by occluding dentinal tubules.

It is another object of the present invention to provide a dental composition capable of occluding a dentinal tubule even when an opening degree of the dentinal tubule is small.

It is a further object of the present invention to provide a dental composition which can relieve hypersensitivity immediately and for a prolonged time and has excellent retention stability.

The above objects and advantages of the present invention can be first attained by a dental composition for relieving dentin hypersensitivity, which comprises (A) a low molecular weight compound which can produce a precipitate that is insoluble or hardly soluble in water when it reacts with a calcium compound.

Further, the above objects and advantages of the present invention can be secondly attained by a dental composition for relieving dentin hypersensitivity, which comprises (A) a low-molecular weight compound which can produce a precipitate that is insoluble or hardly soluble in water when it reacts with a calcium compound, and (B) a calcium compound, and/or (C) an aqueous emulsion containing, as emulsion particles, polymer particles having a diameter smaller than that of a dentinal tubule and forming an agglomerate larger than the diameter of a dentinal tubule when they react with a calcium compound.

The other objects and advantages of the present invention will become apparent from the following detailed description of the invention.

MOST PREFERRED EMBODIMENT FOR PRACTICING THE INVENTION

The component (A) in the present invention is a low molecular weight compound capable of producing a precipitate which is insoluble or hardly soluble in water when it reacts with a calcium compound. Generally speaking, a measure of the water-insoluble or hardly soluble precipitate is preferably that a water-solubility at 25° C. of a calcium salt from the component (A) is less than 0.5 g/100 ml.

The calcium salt formed by the component (A) in the present invention is a salt which is insoluble or hardly soluble in water. Water-insolubility or difficulty of being soluble in water is determined by the presence or absence of a precipitate produced at the time when a solution containing the component (A) and a solution containing a calcium ion are mixed together. The presence or absence of a precipitate can be generally known from the relationship between solubility product and ion product. That is, when an ion product of a calcium salt derived from the component (A) is equal to or larger than a solubility product thereof, the calcium salt is considered as insoluble or hardly soluble in water. As a simple measure for confirming the formation of a precipitate, there is a visual method for observing the formation of a precipitate when an aqueous solution containing a water-soluble organic acid or a water-soluble salt thereof in a concentration range of 1 to 5% by weight and an aqueous solution containing calcium chloride in the same concentration range are mixed together.

In the present invention, the component (A) may be selected from phosphoric acid and phosphoric acid compounds such as phosphoric acid, ammonium phosphate, diammonium hydrogenphosphate, ammonium dihydrogenphosphate, potassium phosphate, dipotassium hydrogenphosphate, potassium dihydrogenphosphate, tribasic sodium phosphate, disodium hydrogenphosphate, sodium dihydrogenphosphate, tribasic lithium phosphate, dilithium hydrogenphosphate, lithium dihydrogenphosphate, alluminum hydrogenphosphate, sodium ammonium hydrogenphosphate, strontium dihydrogenphosphate, barium hydrogenphosphate, magnesium dihydrogenphosphate, hydroxylammonium phosphate and sodium fluoride phosphate; phosphorous acid and phosphorous acid compounds such as phosphorous acid, potassium phosphite, potassium hydrogenphosphite, sodium phosphite, sodium hydrogenphosphite and magnesium hydrogenphosphite; carbonic acid compounds such as ammonium carbonate, potassium carbonate, ammonium hydrogencarbonate, potassium hydrogencarbonate, sodium hydrogencarbonate, magnesium hydrogencarbonate, potassium magnesium hydrogencarbonate, sodium carbonate, potassium carbonate and potassium sodium carbonate; and sulfuric acid and sulfuric acid compounds such as sulfuric acid, ammonium sulfate, ammonium hydrogensulfate, sodium ammonium sulfate, potassium ammonium sulfate, ammonium zinc sulfate, ammonium aluminum sulfate, ammonium cobalt sulfate, ammonium iron sulfate, ammonium copper sulfate and ammonium magnesium sulfate. Among these, sulfuric acid compounds are preferred and ammonium sulfate compounds are particularly preferred. As the measure of water solubility it is preferred that the solubility in water at 25° C. be 0.5 g/100 ml or more.

When the composition of the present invention contains only the component (A), it is preferably a water-soluble or aqueous solution having a concentration of the component (A) in the range of from 1.0% by weight to saturation concentration. The term "aqueous" denotes a water-soluble solution containing water and a solvent which can be mixed with water. Examples of the solvent which can be mixed with water include alcohols such as methanol, ethanol, propanol and isopropyl alcohol; ketones such as acetone and methyl ethyl ketone; ethers such as tetrahydrofuran (THF); amides such as N,N-dimethyl formamide; dimethyl sulfoxide (DMSO); and the like. Among these, ethanol, acetone and DMSO are preferred. Examples of water usable herein include distilled water, ion-exchange water, physiologic saline and the like, and distilled water and ion-exchange water are preferably used. When used in a tooth, water alone or a mixture solution of water and ethanol or acetone is particularly preferred in consideration of toxicity and stimulation to a living body.

In the present invention, when only the component (A) is contained, a thickening agent may be added to the water-soluble or aqueous solution in order to increase the viscosity of the solution. A thickening agent which dissolves or disperses in water or an aqueous solution is preferred, and may be selected from water-soluble polymers such as polyvinyl alcohol, polyvinyl pyrrolidone, polyacrylic acid, metal or ammonium salts thereof, polyethylene glycol, polypropylene glycol, polystyrenesulfonic acid and/or metal salts or ammonium salts of copolymers thereof; polyhydric alcohols such as glycerol and erythritol; and the like.

The calcium compound formed on dentin when it reacts with the component (A) or the components (A) and (B) is a crystal in various forms. It is generally of spherical, relatively roundish oval, laminar or acicular shape. Although its size differs depending on the form of a crystal, a spherical or round crystal has an average diameter of 0.1 to 10 μm, a laminar crystal has an average side length of 0.1 to 10 μm, and an acicular crystal has a thickness of 0.1 to 5 μm and a length of 1 to 10 μm. A calcium salt having such a shape serves to occlude a dentinal tubule as a water insoluble or hardly soluble precipitate which is formed from the component (A) and is formed on the surface of dentin and in a dentinal tubule.

In the present invention, the component (B) is a calcium compound.

Although the component (B) may not be always used in conjunction with the component (A), it has the function of promoting the formation of a water insoluble or hardly soluble precipitate from the component (A) and it itself has the function to occlude dentinal tubules. Therefore, it is desirable that the component (B) be preferably dissolved or dispersed in water or an aqueous solvent. Further, to allow the component (B) to serve to occlude dentinal tubules, it is preferably smaller than the diameter of the dentinal tubule.

The diameter of the dentinal tubule differs among tubules and according to its location and depth, while it is generally in the range of 1 to 3 μm.

The diameter of the dentinal tubule can be measured by observing through a scanning electron microscope (SEM) the surface of dentin exposed by cutting out the enamel of a extracted tooth, the exposed surface of dentin having been brushed with a toothbrush and dentifrice for 1 minute or more and then subjected to ultrasonic cleaning in water.

As the component (B), a water-soluble, insoluble or hardly soluble calcium compound may be used. Illustrative examples of the water-soluble calcium compound include calcium chloride, calcium hypochlorite, calcium nitrate, calcium hydrosulfide, calcium thiocyanide, calcium thiosulfate, calcium iodide and the like. When only the component (A) and a water-soluble compound (B) are used, the component (A) is used in an amount of 50 to 99.9 parts by weight, preferably 60 to 99.9 parts by weight, more preferably 80 to 99.9 parts by weight, based on 100 parts by weight of the total of the components (A) and (B). Illustrative examples of the water-insoluble calcium compound include inorganic calcium compounds such as calcium carbonate, calcium hydroxide, calcium oxide, calcium sulfate, calcium hydrogenphosphate, calcium phosphate and hydroxyapatite; and organic calcium compounds such as calcium formate, calcium acetate, calcium oxalate and calcium tartrate. When only the component (A) and a water insoluble or hardly soluble component (B) are used, the component (A) is used in an amount of 0.5 to 99.9 parts by weight, preferably 10 to 90 part by weight, more preferably 20 to 80 parts by weight, based on 100 parts by weight of the total of the components (A) and (B). A water-soluble calcium compound may be used in combination of a water insoluble or hardly soluble calcium compound.

As for how to use a composition comprising the components (A) and (B), (1) both the components (A) and (B) are mixed together and kept in one container and the resulting mixture is applied to form a coating film, or (2) a composition containing the component (A) kept in a container A and a composition containing the component (B) kept in a container B are applied sequentially in a desired order or mixed together just before use and then applied to form a coating film.

In the above methods (1) and (2), the component (B) is used in such an amount that the water insoluble or hardly soluble precipitate of the component (A) is not allowed to be formed completely before application of the mixture of the components (A) and (B) to the surface of a tooth.

That is, preferably, the component (A) which has not reacted yet with a calcium compound is present before application to the surface of a tooth.

By adjusting the reaction speed between the components (A) and (B) to control the amount of the resulting calcium compound, the amount and crystal size of a water insoluble or hardly soluble compound formed in the dentinal tubule can be controlled.

In this invention, the component (C) is a polymer emulsion (hereinafter sometimes referred to as "latex") prepared by emulsifying or dispersing a natural resin or a synthetic resin into water. The component (C) is characterized in that the emulsified or dispersed polymer comprises emulsion particles having a particle diameter smaller than the size (diameter) of a dentinal tubule and that the polymer emulsion particles can form an agglomerate having a diameter larger than that of a dentinal tubule when they react with a calcium compound.

In order to make an aqueous emulsion penetrate to a depth sufficient for occluding a dentinal tubule, the particle diameter of the emulsion particle of the polymer must be smaller than the diameter of the dentinal tubule. The diameter of a dentinal tubule differs depending on its location and depth and among tubules, but it is generally in the range of 1 to 3 μm. Therefore, the emulsion particles of the polymer of the component (C) have the average particle diameter of preferably 3 μm or less, more preferably 1 μm or less.

The diameter of the dentinal tubule can be measured generally by observing through a scanning electron microscope (SEM) the surface of dentin exposed by cutting out the enamel of an extracted tooth, the exposed surface of dentin having been brushed with a toothbrush and dentifrice for 1 minute or more and then subjected to ultrasonic cleaning in water.

In the emulsion particles of the component (C) there exists a distribution for the particle diameters, and it is not always necessary that all the emulsion particles have a particle diameter smaller than the diameter of a dentinal tubule. Preferably, emulsion particles having a particle diameter of less than 3 μm account for 50% or more by weight of the total of all the emulsion particles of the component (C) and, more preferably, all the emulsion particles have a particle diameter of less than 3 μm. In addition to the above condition, particularly preferably, emulsion particles having a particle diameter of 1 μm or less account for 65% or more by weight, more preferably 75% or more by weight. The object of the present invention can be attained by emulsion particles having the above particle diameter distribution.

The polymer usable as the component (C) of the present invention is selected from homopolymers and copolymers synthesized from radical-polymerizable monomers. Illustrative examples of the radical-polymerizable monomer include conjugated diene monomers such as butadiene and isoprene; aromatic vinyl monomers such as styrene, α-methylstyrene and chlorostyrene; vinyl cyanide monomers such as acrylonitrile and methacrylonitrile; alkyl(meth)

acrylic esters such as methyl(meth)acrylate (hereinafter referred to, like this, as a generic name for acrylic acid and methacrylic acid), ethyl(meth)acrylate and butyl(meth) acrylate; vinyl halides and vinylidenes such as vinyl chloride, vinyl bromide, vinylidene chloride and vinylidene bromide; vinyl esters such as vinyl acetate and vinyl propionate; and the like. These monomers may be used alone or in combination of two or more for polymerization.

Preferably, the polymer synthesized from the above radical-polymerizable monomers is chemically bonded to a functional group which reacts with a calcium compound. The functional group which reacts with a calcium compound is at least one member selected from the group consisting of a carboxyl group, a group having at least one hydroxyl group bonded to a phosphorus atom, and a sulfonic acid group. Methods for introducing the above functional group include a method for introducing a functional group into a polymer, typified by a polystyrene sulfonating method, and a method for hydrolyzing a polymer containing a carboxylate or phosphate. Further, an alternative preferred method is to copolymerize the above radical-polymerizable monomer and a radical-polymerizable monomer having the above functional group or a functional group which can be easily converted into the above functional group in water. Illustrative examples of the radical-polymerizable monomer having a function group which reacts with a calcium compound are given below.

Illustrative examples of the radical-polymerizable monomer having a carboxyl group or a functional group which can be easily converted into a carboxyl group in water include monocarboxylic acids, dicarboxylic acids, tricarboxylic acids and tetracarboxylic acids, and salts and anhydrides thereof, such as (meth)acrylic acid, maleic acid, p-vinylbenzoic acid, 11-(meth)acryloyloxy-1,1-undecanedicarboxylic acid (MAC-10), 1,4-di(meth) acryloyloxyethylpiromellitic acid, 6-(meth) acryloyloxyethylnaphthalene-1,2,6-tricarboxylic-acid, 4-(meth)acryloyloxymethyltrimellitic acid and an anhydride thereof, 4-(meth)acryloyloxyethyltrimellitic acid and an anhydride thereof, 4-(meth)acryloyloxybutyltrimellitic acid and an anhydride thereof, 4-[2-hydroxy-3-(meth) acryloyloxy]butyltrimellitic acid and an anhydride thereof, 2,3-bis(3,4-dicarboxybenzoyloxy)propyl(meth)acrylate, N,O-di(meth)acryloyloxytyrosine, O-(meth) acryloyloxytyrosine, N-(meth)acryloyloxytyrosine, N-(meth)acryloyloxyphenylalanine, N-(meth)acryloyl-p-aminobenzoic acid, N-(meth)acryloyl-O-aminobenzoic acid, 2-, 3- or 4-(meth)acryloyloxybenzoic acid, adduct of 2-hydroxyethyl(meth)acrylate with pyromellitic dianhydride (PMDM), adduct of 2-hydroxyethyl(meth)acrylate with maleic anhydride or 3,3',4,4'-benzophenonetetracarboxylic dianhydride (BTDA) or 3,3', 4,4'-biphenyltetracarboxylic dianhydride, adduct of 2-(3,4-dicarboxybenzoyloxy)1,3-di(meth)acryloyloxypropane, N-phenylglycine or N-tolyl glycine with glycidyl(meth) acrylate, 4-[(2-hydroxy-3-(meth)acryloyloxypropyl)amino] phthalic acid, 3- or 4-[N-methyl-N-(2-hydroxy-3-meth) acryloyloxypropyl)- amino]phthalic acid and the like. Among these, preferred are 11-methacryloyloxy-1,1-undecanedicarboxylic acid (MAC-10) and 4-methacryloyloxyethyltrimellitic acid (4-MET) and an anhydride thereof (4-META).

Preferred examples of the group having at least one hydroxyl group bonded to a phosphorus atom and the functional group which can be easily converted into the above group in water include phosphoric acid ester groups having one or two hydroxyl groups and salts thereof. Illustrative examples of the polymerizable monomer having such a group include 2-(meth)acryloyloxyethylacid phosphate, 2- or 3-(meth)acryloyloxypropylacid phosphate, 4-(meth) acryloyloxybutylacid phosphate, 6-(meth) acryloyloxyhexylacid phosphate, 8-(meth) acryloyloxyoctylacid phosphate, 10-(meth) acryloyloxydecylacid phosphate, 12-(meth) acryloyloxydodecylacid phosphate, bis{2-(meth) acryloyloxyethyl}acid phosphate, bis{2- or 3-(meth) acryloyloxypropyl}acid phosphate, 2-(meth) acryloyloxyethylphenylacid phosphate, 2-(meth) acryloyloxyethyl-p-methoxyphenylacid phosphate and the like. Compounds in which the phosphoric acid group contained in the above compounds is substituted with a thiophosphoric acid group are also included in these examples. Among these, preferred are 2-(meth) acryloyloxyethylphenylacid phosphate and 10- (meth) acryloyloxydecylacid phosphate.

Illustrative examples of the polymerizable monomer having a sulfonic acid group or a functional group which can be easily converted into asulfonic acid group in water include 2-sulfoethyl(meth)acrylate, 2- or 1-sulfo-1 or 2-propyl (meth)acrylate, 1- or 3-sulfo-2-butyl(meth)acrylate, 3-bromo-2-sulfo-2-propyl(meth)acrylate, 3-methoxy-1-sulfo-2-propyl (meth)acrylate, 1,1-dimethyl-2-sulfoethyl (meth)acrylamide, styrene sulfonic acid and salts thereof, of which, 2-methyl-2- (meth)acrylamidepropanesulfonic acid, styrene sulfonic acid and salts thereof are preferred.

The number average molecular weight Mn, measured by a GPC method, of the polymer contained in the component (C) is usually 3,000 or more, preferably 7,000 or more, more preferably 10,000 or more. The upper limit of the number average molecular weight is generally 5,000,000. The component (C) may contain the polymer as an emulsion particle in an amount of 0.1 to 60% by weight, preferably 0.5 to 40% by weight, more preferably 1 to 20% by weight.

The preferred component (C) is an emulsion containing as an emulsion particle a copolymer having alkyl(meth)acrylic ester units comprising 4 to 8 carbon atoms and styrene sulfonic acid units in a molar ratio (alkylacrylic acid ester units to styrene sulfonic acid units) of 50/50 to 99.5/0.5. As such copolymer emulsion, the one proposed in Japanese laid-open patent application publication No. 6-57080 can be used. A preferred example is a component (C) prepared by making emulsion particles of the above copolymer into emulsion particles having a diameter of 3 $\mu$m or less, preferably 1 $\mu$m or less, more preferably 0.5 $\mu$m or less, the most preferably 0.5 $\mu$m or less, with a dispersion grinder such as a high-speed mixer or a homogenizer and containing the resulting emulsion particles in the component (C) in an amount of 0.5% or more by weight. Above all, emulsion particles of the copolymer having a particle diameter of 1.0 $\mu$m or less preferably account for 50% by weight or more, more preferably 75% by weight or more, the most preferably 100% by weight, of the total of emulsion particles.

The emulsion particle having a particle diameter smaller than the diameter of a dentinal tubule, contained in the component (C), is able to form an agglomerate having a diameter larger than that of the dentinal tubule through its reaction with a calcium compound such as calcium chloride, when it is added as the component (B) to the component (C).

When the calcium compound is added in an amount of 10 to 100 parts by weight based on 100 parts by weight of an nonvolatile component contained in the emulsion, the diameter of the agglomerate generally reaches more than 3 $\mu$m, preferably 10 $\mu$m or more, more preferably 50 $\mu$m to several thousands of microns.

Using the component (C) having the above properties in the composition of the present invention, small-sized emulsion particles penetrating into a dentinal tubule react with a calcium ion eluted from hydroxyapatite present in peritubular dentin that mainly forms dentinal tubules, a calcium ion present in a marrow liquid contained in dentin, or the component (B) to form a great number of large agglomerates.

A great number of large agglomerates thus formed form a state (a coating film) in which they are filled continuously in the longitudinal direction of a dentinal tubule. By the formation of such state, the tubule is occluded. The state in which the tubule is occluded is formed quickly by using the component (A) or (B) of the present invention and kept for a prolonged period because adhesion between the agglomerate and dentin is maintained for a long time.

The nonvolatile component is contained in an amount of 0.1 to 60 parts by weight, preferably 0.5 to 40 parts by weight, more preferably 1 to 20 parts by weight, based on 100 parts by weight of the component (C).

As for how to use a composition comprising the components (A) and (C), (1) both the components (A) and (C) are mixed together and kept in one container and the resulting mixture is applied to form a coating film, or (2) a composition containing the component (A) kept in a container A and a composition containing the component (C) kept in a container C are applied sequentially in a desired order or mixed together just before use and then applied to form a coating film.

When the component (A) and only the component (C) are used in the present invention, the component (A) is contained in an amount of 0.01 to 99 parts by weight, preferably 0.1 to 50 parts by weight, more preferably 0.5 to 30 parts by weight, based on 100 parts by weight of the total of the components (A) and (C).

The polymer as an emulsion particle contained in the component (C) is advantageously contained in an amount of 0.1 to 60 parts by weight, preferably 0.5 to 40 parts by weight, more preferably 1 to 20 parts by weight, based on 100 parts by weight of the total of the components (A) and (C).

When, the components (A) and (C) are mixed together, for instance, in the above method (1) and in the above method (2) in which mixing is effected just before use, the component (A) is preferably blended in such an amount that the component (C) is not allowed to agglomerate to a great extent immediately after mixing. When the component (A) agglomerates considerably immediately after mixing, a great number of large agglomerates are formed and hence, emulsion particles cannot penetrate into the inside of the dentinal tubule. As a result, the occlusion degree of the dentinal tubules may decrease.

As for how to use a composition comprising the components (A), (B) and (C), (1) all the components (A), (B) and (C) are mixed together and kept in one container and the resulting mixture is applied to form a coating film, (2) compositions containing the components (A), (B) and (C) are each kept in containers A, B and C, and applied sequentially, or mixed together just before use and the resulting mixture is applied to form a coating film; and (3) a composition containing the components (A) and (C) kept in one container AC and a composition containing the component (B) kept in a container B are applied sequentially, or mixed together just before use and applied to form a coating film.

In the present invention, when all the components (A), (B) and (C) are used, the total amount of the components (A) and (B) is preferably controlled such that the component (C) should be contained in an amount of 50 to 99.9 parts by weight, preferably 70 to 99.9 parts by weight, more preferably 80 to 99.9 parts by weight based on 100 parts by weight of the total of the components (A), (B) and (C).

The previously-mentioned ratio of the component (A) to the component (B) can be applied here. The polymer as an emulsion particle contained in the component (C) is advantageously contained in an amount of 0.1 to 60 parts by weight, preferably 0.5 to 40 parts by weight, more preferably 1 to 20 parts by weight based on 100 parts by weight of the total of the components (A), (B) and (C).

To the dental composition of the present invention may be added an agglomeration promoting agent in a concentration range that does not impair the effect of the present invention. Illustrative examples of the agglomeration promoting agent include inorganic acids such as hydrochloric acid and nitric acid; chlorides and oxides of iron, copper, zinc, strontium, silver and tin; organic acids such as formic acid, acetic acid, lactic acid, citric acid, itaconic acid, maleic acid, succinic acid, malic acid, tannic acid, toluene sulfonic acid, adipic acid, tartaric acid, ascorbic acid, and metal salts thereof; EDTA; and the like. A fluoride such as sodium fluoride or potassium fluoride may also be used as required.

Further studies conducted by the inventors have revealed that the durability of a coating film formed by a composition comprising the components (A) and (B) and/or (C) of the present invention on the surface of dentin is affected by the concentration of metal ions contained in the dispersing medium of an emulsion, and that the higher the concentration of metal ions the lower the durability of the coating film becomes. The inventors have therefore studied the metal ions contained in the dispersing medium of the emulsion and the durability of the coating film and have found that a coating film having excellent durability can be obtained by purifying the emulsion to reduce the concentration of metal ions preferably to 1,000 ppm or less, more preferably 800 ppm or less, the most preferably 500 ppm or less.

To reduce the concentration of metal ions to the above low level, a diafiltration method or a dialysis method can be used. Of these methods, the diafiltration method is preferred.

The diafiltration method is used as one of membrane filtration and membrane separation techniques in food, medicine and other industrial fields. An ultrafiltration apparatus and membrane are described in the *Outline of Membrane Treatment Technology* edited by Hiroshi Shimizu, supervised by Masayuki Nakagai and published by Fuji Technosystem Publication Co.

The apparatus described in the above publication can be used in the present invention. An ultrafiltration apparatus and membrane described in the *Recent Application of Flat Membrane-type Ultrafiltration Apparatus* written by Suguru Higasa and given in the December 1990 issue of Gekkan Food Chemical can also be used. More specifically, PC Cassette System manufactured by Rhone Poulenc can be used. Illustrative examples of a material for a cassette-like membrane include polyacrylonitrile copolymers, polyvinylidene fluoride, sulfonated polysulfone, polyether sulfone and the like, of which, sulfonated polysulfone is preferred.

Water usable to reduce the concentration of metal ions contained in the dispersion medium of the emulsion in the present invention is selected from distilled water, deionized water, purified water and the like. Water called "strongly oxidized water" or "strongly acidic water", obtained by electrolysis of water, can also be used. The above water preferably has a metal ion concentration of 100 ppm or less, more preferably 10 ppm or less, the most preferably 1 ppm or less.

Further, in the present invention, considering that the composition is used in the oral cavity, water which meets to medical and food standards such as water conforming to the standards of the Japanese Pharmacopeia or water approved as a food additive is preferably used.

Surprisingly, it has newly been found that the component (C) of the present invention can suppress the proliferation of microbes in addition to its effect of providing excellent film durability by reducing the concentration of metal ions in the dispersion medium to 1,000 ppm or less. That is, it has been revealed that no growth of mold is observed and further, transplanted mold does not grow by reducing the concentration of metal ions contained in the dispersion medium of the component (C) to 1,000 ppm or less. Growth and proliferation of such microbes as mold are not only insanitary but also readily cause generation of a bad smell and destruction of an emulsion due to the agglomeration of emulsion particles disadvantageously.

To prevent the growth of microbes in the emulsion, an antiseptic component (D) can be used. The term "antiseptic (agent)" is a concept including anti-mold agents.

Antiseptics usable in the present invention are those which can be generally used industrially. However, antiseptics suitable for the purpose of the present invention should be selected from those having low toxicity to the human body and being sanitary and should not impair the effect of relieving hypersensitivity without agglomerating emulsion particles remarkably for a short or long period. Cohesiveness of emulsion particles is greatly affected by the chemical structure and amount of an antiseptic used. Meanwhile, the effect of an antiseptic is greatly affected by the components and composition of a polymer constituting an emulsion, the concentration of components dissolved in the emulsion such as cations and anions, and pH of the emulsion. Therefore, a combination which satisfies the three requirements—toxicity to the human body and sanitation, no agglomeration of emulsion particles and antiseptic effect—should be selected.

Specific examples of the antiseptic component (D) which can be suitably used in the dental composition of the present invention include aliphatic alcohols such as ethanol, n-propanol and isopropanol; halogenated aliphatic alcohols such as chlorobutanol and 2-bromo-2-nitro-propanol-1,3-diol (to be abbreviated as bronopol hereinafter); aromatic alcohols such as 2,4-dichlorobenzyl alcohol, 2-phenoxyethanol, phenoxyisopropanol, phenylethyl alcohol and 3-(4-chlorophenoxy)-1,2-propane diol; aldehydes such as 5-bromo-5-nitro-1,3-dioxane, formaldehyde, paraformaldehyde and glutaraldehyde; gradually-liberating agents capable of forming an aldehyde under acidic condition, such as hexamethylenetetramine, monomethylol dimethyl hydantoin and dimethylol methyl hydantoin; amides such as chloroacetoamide; ureas such as N,N'-methylene-bis(N'-(1-(hydroxymethyl)-2,5-dioxo-4-imidazolidinyl)urea and N-(hydroxymethyl)-N-(1,3-dihydroxymethyl-2,5-dioxo-4-imidazolidinyl)-N'-(hydroxymethyl)urea; inorganic sulfites, bisulfites and pyrosulfites such as sodium sulfite, potassiun sulfite, sodium bisulfite, potassium bisulfite, sodium pyrosulfite and potassium pyrosulfite; inorganic acids such as boric acid; organic acid compounds such as formic acid, propionic acid, 10-undecylenic acid, sorbic acid, benzoic acid, salicylic acid and 2-acetyl-5-hydroxy-3-oxo-4-hexanoic acid δ lactone; antibiotics such as 2,6-diacetyl-7,9-dihydroxy-8,9b-dimethyl-1,3-(2H,9bH)-dibenzoflandion; p-hydroxy benzoate compounds such as methyl p-hydroxy benzoate, ethyl p-hydroxy benzoate, n-propyl p-hydroxy benzoate, n-isopropyl p-hydroxy benzoate, n-butyl p-hydroxy benzoate, n-isobutyl p-hydroxy benzoate, t-butyl p-hydroxy benzoate and benzyl p-hydroxy benzoate; halogenated phenol compounds such as 4-chloro-3-methyl phenol, 4-chloro-3,5-xylenol, 3,4,5,6-tetrabromo-O-cresol, 2,4-dichloro-3,5-xylenol, 2-benzyl-4-chloro-phenol, 2,2'-methylene-bis-(4-chlorophenol), 3,3'-dibromo-5,5'-dichloro-2,2'-dihydroxy-diphenylmethane and 2,2'-methylene-bis(3,4,6-trichlorophenol); phenol compounds such as 4-chloro-5-methyl-2-(1-methylethyl)phenol, 1-methyl-2-hydroxy-4-isopropyl benzene, 2-phenyl phenol and 4-isopropyl-3-methyl-phenol; diphenyl ether compounds such as 2,4,4'-trichloro-2'-hydroxydiphenyl ether; carbonilide compounds such as 3,4,40-trichlorocarbanilide and 4,4'-dichloro-3-(3-fluoromethyl)carbanilide; benzamidine compounds such as 4,4'-diamidino-α,ω-diphenoxypropane isethionate, 4,4'-(trimethylenedioxane)-bis-(3-bromobenzamidine diisethionate (hereinafter referred to as dibromopropamidine) and 1,6-di(4-amidinophenoxy)-n-hexane(hexamidine isethionate); cyclic thiohydroxamic acids and salts thereof such as pyridine-1-oxide-2-thiol-sodium salts, zinc bis-(2-pyridinethiol-1-oxide)bis-(2-pyridylthio)zinc-1,1'-dioxide(zinc pyrithione); N-acetal compounds such as 5-amino-1,3-bis(2-ethylhexyl)-5-methylhexahydropyrimidine(hexsetidine) and tris-hydroxyethylhexahydrotriazine; phthalimide derivatives such as N-(trichloromethylthio)-4-cyclohexane-1,2-dicarboxyimide(captane); o-acetal compounds such as 6acetoxy-2,4-dimethyl-m-dioxane(dimethoxane); oxazolidine compounds such as 4,4-dimethyl-1, 3-oxazolidine (oxazine A); quinoline compounds such as 8-hydroxyquinoline; cationic substances such as bis(p-chlorophenyldiguanide)hexane and polyhexamethyl-enebiguanide hydrochloride; quarterly salt compounds such as alkyltrimethylammonium bromide, N-dodecyl-N,N-dimethylbenzyl ammonium, and N,N-dimethyl-N-(2-(2-(4-(1,1,3,4-tetramethylbutyl)phenoxy)ethoxy)-ethyl)benzene methane ammonium chloride; organic mercury compounds such as ethyl mercury thiosalicylate and phenyl acetate mercury; iodine compounds such as sodium iodate; glyceryl monolaurates; pyridone derivatives such as 1-hydroxy-4-methyl-6-(2,4,4-trimethylpentyl)-2-(1H)pyridone ethanol amine salt; and the like. It is desirable that an antiseptic which does not agglomerate emulsion particles remarkably or does not impair occlusion of dentinal tubules is selected from among these antiseptics.

An antiseptic suitably used in combination with an emulsion of a copolymer of alkyl(meth)acrylate and styrene sulfonic acid is 2-phenoxy ethanol, benzoic acid or phenethyl alcohol. As for toxicities of these antiseptics and anti-mold agents, benzoic acid has been finally allowed for use in cosmetics and 2-phenyl alcohol and phenethyl alcohol have been provisionally allowed for use in cosmetics (please refer to "COSMETIC AND DRUG PRESERVATION, PRINCIPLES AND PRACTICE" edited by Jon J. Kabara, published by Fragrance Journal Co.).

The amount of the antiseptic component (D) differs according to the compound and emulsion used, while it is generally used in an amount of 0.01 to 50 parts by weight, preferably 0.01 to 20 parts by weight, most preferably 0.01 to 10 parts by weight, based on 100 parts by weight of the total of the components (C) and (D).

EXAMPLES

The present invention is explained in more detail hereinafter with reference to the following examples. However, the invention is not limited to these examples.

(Preparation of a hypersensitive dentin model)

A bovine anterior tooth which was extracted and frozen for preservation was thawed just before use, and a dentin plate of about 10×10×2 mm was cut out from the anterior tooth with a low-speed rotary diamond cutter (ISOMET, BUHLER) under injection of water. One side surface of the dentin plate was brushed with a toothbrush (GUM manufactured by Butler Co.) having dentifrice (WHITE SUN-STAR F manufactured by Sunstar Inc.) thereon with a force of 20 to 30 g/cm$^2$ for about 2 to 3 minutes under injection of water. After fully washing with water, an ultrasonic wave was applied to the dentin plate in water for 10 minutes for washing to prepare a brushed surface as a hypersensitive dentin model. Thereafter, it was preserved in water until it was used in the following experiments. But, the thus prepared hypersensitive dentin model was used within 24 hours.

(Method for evaluating the effect of relieving hypersensitivity)

Apparent water was removed from the surface of the hypersensitive dentin model taken out from water and dried by an air blow. One sponge ball (sponge provided as an accessory of Super Bond C&B, size S) was picked up by tweezers and fully impregnated with the dental composition of the present invention to apply the composition to the surface of the hypersensitive dentin model. The model was left to stand for 20 seconds and dried by an air blow in such a manner that the liquid was not scattered away. A coating film for relieving dentin hypersensitivity was thus formed.

The hypersensitive dentin model having the coating film formed thereon was treated under the conditions (i) or (ii):

(i) it was subjected to an ultrasonic wave in water for 5 minutes, or (ii) it was brushed with a toothbrush 1,000 times with a load of 100 g under injection of water and washed with water. Thereafter, the occlusion of dentinal tubules was observed through a 1,000× scanning electron photomicrograph (SEM). The occlusion of dentinal tubules was evaluated by the occlusion degree of dentinal tubules represented by the following equation.

Occlusion degree of dentinal tubules (%)=(Number of occluded dentinal tubules/Total number of dentinal tubules observed)×100

Yoshiyama et al. calculated an opening degree of dentinal tubules in J. Dent. Res. 68(11), pp.1498–1502, November, 1989 and reported that about 75% of dentinal tubules having hypersensitivity were open whereas only about 25% of dentinal tubules free from hypersensitivity were open. Evaluation was made based on this report. That is, it is evaluated that when the occlusion degree of dentinal tubules in the present invention was about 75% or more, dentin hypersensitivity was sufficiently relieved, while when the occlusion degree was about 25% or less, dentin hypersensitivity was not relieved.

(Synthesis example of an aqueous polymer emulsion)

50 ml of distilled water was heated to 60° C. and bubbled with a nitrogen gas for 1 hour. Under a nitrogen atmosphere, 2.0 g of methyl methacrylate (MMA), 0.54 g of sodium styrene sulfonate (SSNa), 30 mg of potassium persulfate and 10 mg of sodium hydrogen sulfite were added to the distilled water and stirred violently at 60° C. for 2.5 hours. Further, 1.0 g of MMA, 15 mg of potassium persulfate and 7 mg of sodium hydrogen sulfite were added four times at intervals of 30 minutes and then further stirred violently for 19.5 hours. The resulting mixture was then cooled to room temperature, and 0.19 ml of concentrated hydrochloric acid was added to the mixture and stirred for 2 hours. The mixture was then charged into a dialysis tube to repeat dialysis while the distilled water was exchanged every day during 5 days. This tube was dried at normal temperature under normal pressure to obtain an emulsion having a solid content of 10.9% by weight. It was found from elemental analysis that the MMA unit content of this polymer was 96.9 mol %. When the thus obtained polymer was analyzed by GPC using, as a standard sample, methyl polymethacrylate whose molecular weight was known, its number average molecular weight (Mn) was found to be 1.0×10$^6$. It was confirmed by observation through a transmission microscope that this emulsified polymer emulsion particles had a particle diameter in the range of 0.1 to 0.5 µm and it was also confirmed by laser diffraction/scattering type particle size distribution measuring instrument (LA-910 manufactured by Horiba) that all the polymer emulsion particles had a particle diameter of 1 µm or less. This emulsion is referred to as MSE hereinafter.

The above emulsion MSE was diluted with distilled water and an equivalent amount of an aqueous solution having 1% by weight of calcium chloride as a calcium compound dissolved therein was added to the emulsion MSE containing 5% by weight of a nonvolatile component and stirred. Thereafter, the particle diameter of the resulting mixture was similarly measured by the LA-910 laser diffraction/scattering type particle size distribution measuring instrument. It was found that the polymer emulsion particles present in the emulsion MSE agglomerated and the diameters of the agglomerates are in the wide range of 0.1 to 700 µm with peaks at about 0.3 µm and about 40 µm.

Example 1

An aqueous solution containing 30% by weight of ammonium sulfate was used as the dental composition of the present invention. As a result, the occlusion degree of dentinal tubules in the condition (i) was 90% and that in the condition (ii) was about 80%.

Example 2

To prepare the dental composition of the present invention, 0.05 g of an aqueous solution containing 10% by weight of ammonium sulfate (solution A) and 0.05 g of an aqueous solution containing 1% by weight of calcium chloride (solution B) were mixed together just before use and the composition was used within 30 seconds after mixing. As a result, the occlusion degree of dentinal tubules in the condition (i) was 100% and that in the condition (ii) was about 95%.

Example 3

To prepare the dental composition of the present invention, an aqueous solution containing 5% by weight of a polymer (MSE) and an aqueous solution containing 1% by weight of ammonium sulfate were kept in separate containers, 0.05 g portions were taken from these containers and fully mixed together just before use, and the composition thus prepared was used within 1 minute after mixing. As a result, the occlusion degree of dentinal tubules in the condition (i) was 100% and that in the condition (ii) was about 95%.

Example 4

To prepare the dental composition of the present invention, an aqueous solution containing 2.5% by weight of a polymer (MSE) and 1% by weight of ammonium sulfate and an aqueous solution containing 0.5% by weight of calcium chloride were kept in separate containers, 0.05 g portions were taken from these containers and fully mixed together just before use, and the composition thus prepared was used within 1 minute after mixing. As a result, the occlusion degrees of dentinal tubules both in the conditions (i) and (ii) were 100%.

Example 5

The dental composition of Example 4 was applied to 20 volunteer patients who had an affected part of a tooth worn by excess use of a toothbrush and suffered from dentin hypersensitivity which induced mainly cold water pain sensation. Since the surface of dentin was relatively clean, it was dried by a mild air blow and then coated with the dental composition of Example 4 in the same manner as in Example 4 to form a coating film. As a result, all the patients did not feel cold water pain sensation immediately after the application and even after the lapse of about three months.

Example 6

The dental composition of Example 4 was applied to 10 volunteer patients who had an affected part of a dental root exposed by regression of the gum suffered from dentin hypersensitivity which induced mainly a cold water pain sensation. Since the surface of dentin was relatively clean, it was dried by a mild air blow and coated with the dental composition of Example 4 in the same manner as in Example 4 to form a coating film. As a result, all the patients did not feel a cold water pain sensation immediately after the application and during about the past three months.

Comparative Example 1

Example 1 was repeated without using the dental composition of the present invention and the occlusion degree of dentinal tubules in the conditions (i) and (ii) were checked and found to be 0% for both treatments (i) and (ii). That is, all dentinal tubules were open.

Comparative Example 2

An aqueous solution containing 30% by weight of calcium chloride was used as a composition comprising only the component (B) in place of the dental composition of the present invention in Example 2. As a result, the occlusion degree of dentinal tubules in the condition (i) was about 10% and that in the condition (ii) was 0%.

Comparative Example 3

MSE containing 5% by weight of a high molecular weight polymer was used as a composition comprising only the component (C) in place of the dental composition of the present invention in Example 3. As a result, the occlusion degree of dentinal tubules in the condition (i) was about 10% and that in the condition (ii) was 0%. Almost all the dentinal tubules were open.

Comparative Example 4

An aqueous solution containing 5% by weight of MSE of Comparative Example 3 was used in place of the dental composition of the present invention in Example 3. That is, in accordance with Example 3, the above aqueous MSE solution was applied to 5 volunteer patients who had an affected part of a dental root exposed by regression of the gum and suffered from dentin hypersensitivity which induced mainly a cold water pain sensation. As a result, four out of the five patients did not feel hypersensitivity because the cold water pain sensation was eased immediately after the application but they had a relapse of dentin hypersensitivity about three or four days later. As for the remaining one patient, the effect of relieving hypersensitivity was not observed even immediately after the application, from which it was revealed that the sufficient application effect was not obtained for the dental root.

Example 7

The procedure of the above Emulsion Synthesis Example was repeated to synthesize an emulsion except that a diafiltration apparatus was used in place of a dialysis tube. An ultrafiltration apparatus (PC Cassette System manufactured by Rhone Poulenc) and a sulfonated polysulfone membrane (IRIS3026) were used as the diafiltration apparatus to purify the emulsion at a dilution rate of up to 5 times. In this case, the diafiltration conditions could be effected within the use conditions of the present apparatus. The experiments were carried out while water was added at a membrane area of 0.506 $m^2$ and an average operation pressure of 0.5 to 3 $kgf/cm^2$. The same ultrafiltration apparatus and filtration membrane were also used in the following experiments. The emulsion was diluted with distilled water to a nonvolatile component concentration of 5% by weight. A portion of the thus obtained sample was taken out, emulsion particles were filtrated with the ultrafiltration apparatus, and the concentration of metal ions in the filtrate was measured using a desk-top type plasma emission spectroscopic analyzer (SPS7700, manufactured by Seiko Denshi Kogyo Co.). The same measuring instrument was also used in the following experiments. Most of the measured metal ions contained in the dispersing medium were sodium and potassium ions derived from the monomers and the polymerization initiator, and other metal ions were hardly detected. Therefore, only sodium and potassium ions was determined. The concentration of metal ions (Na+K) was found to be 230 ppm. The emulsion was transferred to a plastic container with a lid and kept in the dark at room temperature for about 3 months. As a result, no growth of mold was observed. The container used for observation was cleaned with ethanol and dried beforehand to eliminate the effects of microbes adhered to the container. The containers used in the following experiments were also cleaned before use.

The emulsion containing 5% by weight of a polymer prepared above and an aqueous solution of 1% by weight of ammonium sulfate were kept in separate containers, and 0.05 g portions were taken out from each of these containers and mixed together just before use. The dental composition of the present invention thus prepared was used within 1 minute after mixing to carry out evaluation on the effect of relieving hypersensitivity and durability. As a result, occlusion degrees of dentinal tubules in the conditions (i) and (ii) were all 100% and that after 35 minutes of ultrasonic cleaning (hereinafter, referred to as condition (iii)) in place of 5 minutes of ultrasonic cleaning in the condition (i) was about 20%.

In the condition (ii), the toothbrush abrasion resistance of a coating film formed on the surface of dentin and the occlusion of dentinal tubules can be checked. However, since the diameter of the hair of a toothbrush is generally 100 to 400 $\mu$m, the occlusion durability of a coating film formed within a dentinal tubule cannot be evaluated. Under the circumstances, though there is no actual case of irradiation of ultrasonic waves, 35 minutes of an ultrasonic exposure test (treatment (iii)) was made as a measure to evaluate the occlusion durability of the inside of a dentinal tubule.

Experiments on Growth of Mold and Experiments on Applicability of Antiseptics

Run No. 1

An emulsion newly synthesized in the same manner as in Emulsion Synthesis Example and purified with a dialysis tube was diluted with distilled water to a nonvolatile component concentration of 5% by weight. A portion of the thus obtained sample was taken out, and emulsion particles thereof were measured for the concentration of metal ions in the filtrate in the same manner as in Example 7. The concentration of metal ions (Na+K) was found to be 1,200 ppm. As a result, the emulsion was transferred to a plastic container with a lid and kept in the dark at room temperature for about 3 months. Black mold as large as 0.1 to 3 mm grew at many places in the emulsion.

Run No. 2

The emulsion, immediately after purification, of Run No.1 containing 5% by weight of the polymer and an aqueous solution of 1% by weight of ammonium sulfate were kept in separate containers, and 0.05 g portions were each taken out from these containers and mixed together just before use. The dental composition of the present invention thus prepared was used within 1 minute after mixing to carry out evaluation on the effect of relieving hypersensitivity and durability. As a result, occlusion degrees of dentinal tubules after treatments (i) and (ii) were all 100% and that after treatment (iii) was 0%.

Run No. 3

An emulsion newly synthesized in the same manner as in Emulsion Synthesis Example and purified with a dialysis tube was diluted with distilled water to a nonvolatile component concentration of 5% by weight. A portion of the thus obtained sample was taken out, and emulsion particles thereof were measured for the concentration of metal ions in the filtrate in the same manner as in Example 7. As a result, the concentration of metal ions (Na+K) was found to be about 300 ppm. The emulsion was transferred to a plastic container with a lid and kept in the dark at room temperature for about 3 months. Black mold as large as 0.1 to 3 mm grew at several places in the emulsion.

Run No. 4

An emulsion was newly synthesized in the same manner as in Emulsion Synthesis Example and purified at a dilution rate of 0.3 time using a diafiltration apparatus. The emulsion was diluted with distilled water to a nonvolatile component concentration of 5% by weight. A portion of the thus obtained sample was taken out, and emulsion particles thereof were measured for the concentration of metal ions in the filtrate in the same manner as in Example 7. The concentration of metal ions (Na+K) was found to be about 1,500 ppm. The emulsion was transferred to a plastic container with a lid and kept in the dark at room temperature for about 3 months. As a result, no growth of mold was observed. The results of evaluation on the effect of relieving hypersensitivity and evaluation on the durability of a coating film were all about 80% in experiments of the conditions (i) and (ii) while 0% in that of the condition (iii). The effect of preventing the growth of mold obtained by using a diafiltration apparatus was confirmed by comparison between this run and Run No. 3. However, the durability of the resulting coating film was insufficient.

Run No. 5

An emulsion was newly synthesized in the same manner as in Emulsion Synthesis Example and purified at a dilution rate of 2 times using a diafiltration apparatus. The emulsion was diluted with distilled water to a nonvolatile component concentration of 5% by weight. A portion of the thus obtained sample was taken out, and the concentration of metal ions in the filtrate was measured in the same manner as in Example 7. The concentration of metal ions (Na+K) was found to be about 970 ppm. The emulsion was transferred to a plastic container with a lid and kept in the dark at room temperature for about 3 months. As a result, no growth of mold was observed. The results of evaluation on the effect of relieving hypersensitivity and evaluation on durability were all about 90% in the experiments (i) and (ii) and about 20% in the experiment (iii). Improvement in the durability of the resulting coating film by reducing the concentration of metal ions in the dispersing medium was confirmed by comparison between this run and Run No. 4.

Run No. 6

An emulsion was newly synthesized in the same manner as in Emulsion Synthesis Example and purified at a dilution rate of 5 times using a diafiltration apparatus. The emulsion was diluted with distilled water to a nonvolatile component concentration of 5% by weight. A portion of the thus obtained sample was taken out, and emulsion particles thereof were measured for the concentration of metal ions in the filtrate in the same manner as in Example 7. The concentration of metal ions (Na+K) was found to be about 300 ppm. The emulsion was transferred to a plastic container and kept in the dark at room temperature for about 3 months. As a result, no growth of mold was observed. The results of evaluation on the effect of relieving hypersensitivity and evaluation on durability were all 100% after treatments (i) and (ii) and about 20% after treatment (iii).

Run No. 7

A 10 g portion of the emulsion (metal ions: 970 ppm) of Run No. 5 was put into three 20 cc brown glass bottles with a plastic screw lid as a sample to three samples for the emulsion. Further, mold grown in the emulsion of Run No. 1 was cut into 1 to 2 mm pieces and each piece was transplanted to each sample. After measuring the size of the mold with calipers, the mold was left to stand in the dark at room temperature for 2 months. As a result, the mold in one out of the three samples grew about 25% bigger, but the mold in the other two samples remained unchanged in size. This indicates that growth of microbes such as mold can be suppressed even when they have entered the emulsion after diafiltration.

Run No. 8

A 10 g portion of the emulsion (metal ions: 300 ppm) of Run No. 6 was put into three 20 cc brown glass bottles with a plastic screw lid as a sample to prepare three samples for the emulsion Further, mold grown in the emulsion of Run No. 1 was cut into 1 to 2 mm pieces and each piece was transplanted to each sample. After measuring the size of the mold with calipers, the mold was left to stand in the dark at room temperature for 1 to 2 months. As a result, the mold in all the three samples remained unchanged in size.

Run No. 9

A 10 g portion of the emulsion (metal ions: 1,500 ppm) of Run No. 4 was put into three 20 cc brown glass bottles with a plastic screw lid as a sample to prepare three samples for the emulsion. Further, mold grown in the emulsion of Run No. 1 was cut into 1 to 2 mm pieces and each piece was transplanted to each sample. After measuring the size of the mold with calipers, the mold was left to stand in the dark at room temperature for 1 to 2 months. As a result, the mold in all the three samples grew bigger by 10 to 50%. This indicates that microbes such as mold grow when they have entered the emulsion after diafiltration and impair sanitation in the composition of the present invention, disadvantageously.

Run No. 10

To the emulsion (metal ions: 1,500 ppm) of Run No. 4 was added 3% by weight of 2-phenyl alcohol as an antiseptic, and mold was transplanted to the emulsion and left to stand in the dark at room temperature for 1 month as in Run No. 7. No size expansion of the mold was observed in all the samples and the emulsion remained unchanged in state.

Run No. 11

To the emulsion (metal ions: 1,500 ppm) of Run No. 4 was added 0.3% by weight of benzoic acid as an antiseptic, and mold was transplanted to the emulsion and left to stand in the dark at room temperature for 1 month as in Run No. 7. No size expansion of the mold was observed in all the samples and the emulsion remained unchanged in state.

Run No. 12

To the emulsion (metal ions: 1,500 ppm) of Run No. 4 was added 2% by weight of phenethyl alcohol as an antiseptic, and mold was transplanted to the emulsion and left to stand in the dark at room temperature for 1 month as in Run No. 7. No size expansion of the mold was observed in all the samples and the emulsion remained unchanged in state.

Run No. 13

To the emulsion (metal ions: 1,500 ppm) of Run No. 4 was added 0.5% by weight of salicylic acid as an antiseptic, but the salicylic acid did not dissolve in the emulsion.

Run No. 14

To the emulsion (metal ions: 1,500 ppm) of Run No. 4 was added 0.5% by weight of formaldehyde as an antiseptic, but the emulsion agglomerated within 1 week.

Run No. 15

To the emulsion (metal ions: 1,500 ppm) of Run No. 4 was added 0.5% by weight of glutaraldehyde as an antiseptic, but the emulsion agglomerated within 1 week.

Run No. 16

To the emulsion (metal ions: 1,500 ppm) of Run No. 4 was added 0.5% by weight of zinc-bis-(2-pyridinethiol-1-oxide)bis-(2-pyridylthio)zinc-1,1'-dioxide(zinc pyrithione) as an antiseptic, but the emulsion agglomerated immediately.

We claim:

1. A dental composition for relieving dentin hypersensitivity, which comprises (A) ammonium sulfate as a low molecular weight compound capable of producing a precipitate which is insoluble or hardly soluble in water when it reacts with a calcium compound; and (C) an aqueous emulsion, said aqueous emulsion containing, as emulsion particles, polymer particles having a diameter smaller than that of a dentinal tubule and forming an agglomerate larger than the diameter of a dentinal tubule when they react with a calcium compound, and the metal ion concentration of said aqueous emulsion being 1,000 ppm or less in a dispersing medium.

2. The dental composition according to claim 1, wherein the aqueous emulsion (C) is contained in an amount of 0.01 to 99 parts by weight based on 100 parts by weight of the total of the components (A) and (C).

3. The dental composition according to claim 1, wherein said aqueous emulsion (C) is a polymer emulsion prepared by an emulsion polymerization which comprises (a) repeating units derived from a (meth)acrylate ester and (b) repeating units derived from a vinyl compound having a group —$SO_3R$ wherein R represents a hydrogen atom, an alkali-metal atom or an ammonium ion, the molar ratio of the (meth)acrylate ester to the vinyl compound being from 99:1 to 50:50.

4. The dental composition according to claim 3, wherein said polymer emulsion further comprises (c) repeating units derived from a vinyl compound having a group —$COOR_4$ wherein $R_4$ represents a hydrogen atom, an alkali-metal atom or an ammonium ion or a group —$OPO(OR_6)_2$ wherein $R_6$ represents a hydrogen atom, an alkali-metal atom or an ammonium ion, the molar ratio of the (meth)acrylate ester to the total of the vinyl compound having a group —$SO_3R$ and the vinyl compound having a group —$COOR_4$ or —$OPO(OR_6)_2$ being from 99:1 to 50:50.

5. The dental composition according to claim 4, wherein the molar ratio of the vinyl compound having a group —$SO_3R$ to the compound having a group —$COOR_4$ or —$OPO(OR_6)_2$ is from 99:1 to 1:99.

6. The dental composition according to claim 1, wherein the aqueous emulsion (C) has been purified by diafiltration to reduce the metal ion concentration in the dispersing medium to 1,000 ppm or less.

7. The dental composition according to claim 1, wherein the component (A) has a concentration in the range of 1.0% by weight to saturation and is in the form of a water-soluble solution or an aqueous solution.

8. The dental composition according to claim 1, wherein the polymer is contained in the component (C) in an amount of 0.1 to 60 parts by weight based on 100 parts by weight of the dental composition containing the component (C).

9. The dental composition according to claim 1, wherein the emulsion particles of the polymer contained in the component (C) include particles having a diameter of 3 μm or less.

10. The dental composition according to claim 1, wherein the polymer contained in the component (C) has at least one functional group, which is capable of reacting with a calcium compound, selected from the group consisting of a carboxyl group, a group having at least one hydroxyl group bonded to a phosphorus atom and a sulfonic acid group.

11. The dental composition according to claim 1, wherein the component (C) is an emulsion of a copolymer containing alkyl (meth)acrylate and styrene sulfonic acid.

12. The dental composition according to claim 1, wherein said aqueous emulsion (C) is an emulsion containing as an emulsion particle a copolymer having alkyl (meth)acrylic ester units comprising 4 to 8 carbon atoms and styrene sulfonic acid units in a molar ratio of alkyl (meth)acrylic acid ester units to styrene sulfonic acid units of 50/50 to 99.5/0.5.

13. The dental composition according to claim 1, which further contains (D) at least one antiseptic selected from inorganic and organic antiseptics.

14. A dental composition for relieving dentin hypersensitivity, which comprises (A) ammonium sulfate as a low molecular weight compound capable of producing a precipitate which is insoluble or hardly soluble in water when it reacts with a calcium compound, and (B) a calcium compound, and (C) an aqueous emulsion containing, as emulsion particles, polymer particles having a diameter smaller than that of a dentinal tubule and forming an agglomerate larger than the diameter of a dentinal tubule when they react with a calcium compound, the metal ion concentration of the aqueous emulsion (C) being 1,000 ppm or less in a dispersing medium.

15. The dental composition according to claim 14, wherein the aqueous emulsion (C) has been purified by diafiltration to reduce the metal ion concentration in the dispersing medium to 1,000 ppm or less.

16. The dental composition according to claim 14, wherein the component (A) is contained in an amount of 99.99 parts by weight or less, the component (B) in an amount of 99.99 parts by weight or less, and the component (C) in an amount of 0 to 99.99 parts by weight, based on 100 parts by weight of the total of the components (A), (B) and (C).

17. The dental composition according to claim 14, wherein the component (A) has a concentration in the range of 1.0% by weight to saturation and is in the form of a water-soluble solution or an aqueous solution.

18. The dental composition according to claim 14, wherein the component (B) is calcium chloride.

19. The dental composition according to claim 14, wherein the component (B) is calcium chloride, has a concentration in the range of 0.01% by weight to saturation concentration and is in the form of a water-soluble solution or an aqueous solution which may contain an organic solvent.

20. The dental composition according to claim 14, wherein the polymer is contained in the component (C) in an amount of 0.1 to 60 parts by weight based on 100 parts by weight of the dental composition containing the component (C).

21. The dental composition according to claim 14, wherein the emulsion particles of the polymer contained in the component (C) include particles having a diameter of 3 $\mu$m or less.

22. The dental composition according to claim 14, wherein the polymer contained in the component (C) has at least one functional group, which is capable of reacting with a calcium compound, selected from the group consisting of a carboxyl group, a group having at least one hydroxyl group bonded to a phosphorus atom and a sulfonic acid group.

23. The dental composition according to claim 14, wherein the component (C) is an emulsion of a copolymer containing alkyl (meth)acrylate and styrene sulfonic acid.

24. The dental composition according to claim 14, wherein said aqueous emulsion (C) is an emulsion containing as an emulsion particle a copolymer having alkyl (meth) acrylic ester units comprising 4 to 8 carbon atoms and styrene sulfonic acid units in a molar ratio of alkyl (meth) acrylic acid ester units to styrene sulfonic acid units of 50/50 to 99.5/0.5.

25. The dental composition according to claim 14, which further contains (D) at least one antiseptic selected from inorganic and organic antiseptics.

26. The dental composition according to claim 14, wherein said aqueous emulsion (C) is a polymer emulsion prepared by an emulsion polymerization which comprises (a) repeating units derived from a (meth)acrylate ester and (b) repeating units derived from a vinyl compound having a group —$SO_3R$ wherein R represents a hydrogen atom, an alkali-metal atom or an ammonium ion, the molar ratio of the (meth)acrylate ester to the vinyl compound being from 99:1 to 50:50.

27. The dental composition according to claim 26, wherein said polymer emulsion further comprises (c) repeating units derived from a vinyl compound having a group —$COOR_4$ wherein $R_4$ represents a hydrogen atom, an alkali-metal atom or an ammonium ion or a group —$OPO(OR_6)_2$ wherein $R_6$ represents a hydrogen atom, an alkali-metal atom or an ammonium ion, the molar ratio of the (meth)acrylate ester to the total of the vinyl compound having a group —$SO_3R$ and the vinyl compound having a group —$COOR_4$ or —$OPO(OR_6)_2$ being from 99:1 to 50:50.

28. The dental composition according to claim 27, wherein the molar ratio of the vinyl compound having a group —$So_3R$ to the compound having a group —$COOR_4$ or —$OPO(OR_6)_2$ is from 99:1 to 1:99.

29. A method for relieving dentin hypersensitivity comprising applying a composition comprising (A) ammonium sulfate as a low molecular weight compound capable of producing a precipitate which is insoluble or hardly soluble in water when it reacts with a calcium compound and (C) an aqueous emulsion, said aqueous emulsion containing, as emulsion particles, polymer particles having a diameter smaller than that of a dentinal tubule and forming an agglomerate larger than the diameter of a dentinal tubule when they react with a calcium compound, the metal ion concentration of said aqueous emulsion being 1,000 ppm or less in a dispersing medium, to an exposed surface of dentin.

30. The method according to claim 29, wherein said composition further comprises a calcium compound (B) and said calcium compound is water-soluble.

31. The method according to claim 29, wherein said composition further comprises a calcium compound (B) and said calcium compound is water insoluble or hardly soluble.

32. The method according to claim 29, wherein said aqueous emulsion (C) is contained in an amount of 0.01 to 99 parts by weight based on 100 parts by weight of the total of the components (A) and (C).

33. The method according to claim 29, wherein said composition further comprises a calcium compound (B) and the aqueous emulsion (C) is contained in an amount of 50 to 99.9 parts by weight based on 100 parts by weight of the total of the components (A), (B) and (C).

34. The method according to claim 29, wherein said aqueous emulsion (C) is a polymer emulsion prepared by an emulsion polymerization which comprises (a) repeating units derived from a (meth)acrylate ester and (b) repeating units derived from a vinyl compound having a group —$SO_3R$ wherein R represents a hydrogen atom, an alkali-metal atom or an ammonium ion, the molar ratio of the (meth)acrylate ester to the vinyl compound being from 99:1 to 50:50.

35. The method according to claim 34, wherein said polymer emulsion further comprises (c) repeating units derived from a vinyl compound having a group —$COOR_4$ wherein $R_4$ represents a hydrogen atom, an alkali-metal atom or an ammonium ion or a group —$OPO(OR_6)_2$ wherein $R_6$ represents a hydrogen atom, an alkali-metal atom or an ammonium ion, the molar ratio of the (meth)acrylate ester to the total of the vinyl compound having a group —$SO_3R$ and the vinyl compound having a group —$COOR_4$ or —$OPO(OR_6)_2$ being from 99:1 to 50:50.

36. The method according to claim 35, wherein the molar ratio of the vinyl compound having a group —$SO_3R$ to the compound having a group —$COOR_4$ or —$OPO(OR_6)_2$ is from 99:1 to 1:99.

37. The method according to claim 29, wherein the aqueous emulsion (C) has been purified by diafiltration to reduce the metal ion concentration in the dispersing medium to 1,000 ppm or less.

* * * * *